July 22, 1952 E. S. BOERNER Plant Pat. 1,114
ROSE PLANT
Filed May 28, 1951
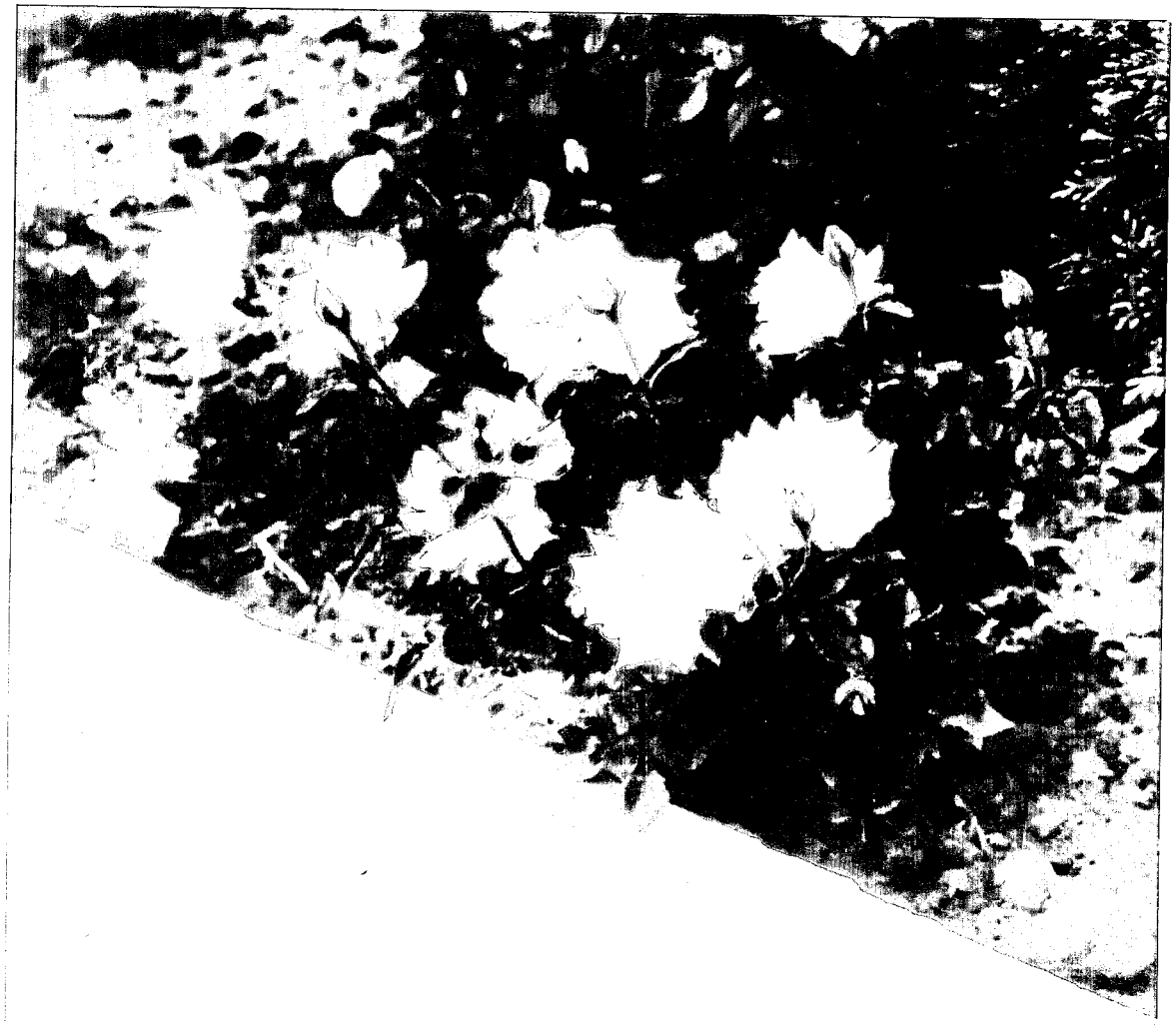
Inventor.
E. S. Boerner
By: Robert Cobb
Attorneys.

Patented July 22, 1952

Plant Pat. 1,114

UNITED STATES PATENT OFFICE 1,114

ROSE PLANT

Eugene S. Boerner, Newark, N. Y., assignor to Jackson & Perkins Company, Newark, N. Y., a corporation of New York Application May 28, 1951, Serial No. 228,592

1 Claim. (Cl. 47—61)

The present invention relates to a new and distinct variety of rose plant of the large-flowered polyantha class, originated by me by crossing an unnamed and unpatented yellow Floribunda seedling [derived from an unnamed and unpatented climber × "Golden Main" (Plant Patent No. 254)] with an unnamed and unpatented low-growing yellow Floribunda.

The primary objective in making this cross was to intensify the color of the first-mentioned yellow Floribunda parent, while at the same time producing improvements over the low-growing yellow Floribunda parent, including the attainment of a truly dwarf habit of growth.

The particular seedling which resulted from this breeding fully achieved this objective in a marked and striking way, as evidenced by the following important and outstanding characteristics which constitute a unique combination by which the present variety is definitely distinguished from its parents, as well as from all other roses of its class:

(1) Dwarf habit of plant growth, combined with hybrid tea-shaped buds and flowers which have heretofore been unknown in dwarf-growing roses;

(2) Golden yellow color of the flowers, which may be more specifically described as Empire Yellow in general tonality;

(3) Long-lasting quality of the flowers on the bush outdoors;

(4) Exceptionally large size of the flowers for a dwarf plant, said flowers averaging about 2½ inches in diameter;

(5) Consistent blooming habit which makes this variety exceptional and especially desirable for border plantings.

Asexual reproduction of the new variety by budding at Newark, New York, and at Pleasanton, California, shows that the foregoing characteristics come true to form and are established and transmitted through succeeding propagations.

The accompanying drawing shows a specimen of the new variety, with the flowers and foliage in different stages of development.

The following is a detailed description of the new variety, with color terminology in accordance with Ridgway's Color Standards and Nomenclature:

Parentage: Seedling.

*Seed parent.*—An unnamed yellow Floribunda seedling (unnamed climber × "Golden Main").

*Pollen parent.*—An unnamed low-growing yellow Floribunda.

Classification:

*Botanic.*—Large-flowered polyantha.

*Commercial.*—Floribunda.

*Flower*

(Observations made at Newark, New York, in the garden about mid-morning in the early part of the month of September.)

Blooming habit: Recurrent—continuous.

Bud:

*Size.*—Small.

*Form.*—Ovoid. Is not affected by wet or hot weather.

*Color.*—When sepals first divide—Scarlet, Plate 1. When petals begin to unfurl—upper half of petals: Spectrum Red, Plate 1; lower half of petals: Lemon Yellow, Plate 4. When half blown—inside of petals: Lemon Chrome, Plate 4; reverse of petals: Empire Yellow, Plate 4, with upper half of petals lightly overcast with Spectrum Red, Plate 1.

*Sepals.*—Slightly branched; curl back when petals begin to unfurl. Color—inside: Light Lumiere Green, Plate 17; outside: Biscay Green, Plate 17.

*Calyx.*—Shape—pear. Size—small. Aspect—smooth. Odor when rubbed—none. Color—Spinach Green, Plate 5.

*Peduncle.*—Length—short. Aspect—smooth. Color—Oil Green, Plate 5. Strength—erect; slender.

*Opening.*—Bud opens up well. Is not affected by adverse weather conditions.

Bloom:

*Size.*—Medium. Average size when fully expanded—2½ inches.

*Borne.*—Singly and several together.

*Stems.*—Medium length; normal strength.

*Form.*—When first open—high center. Permanence—flattens.

*Petalage.*—Double (full but open center). Number of petals under normal conditions—25 to 30.

(Description made from a freshly opened bloom cut early in the morning and taken indoors or in shade.)

*Color.*—Center of flower—Empire Yellow, Plate 4. Outer petals—Pinard Yellow, Plate 4. Base of petals (aiglet)—Lemon Yellow, Plate 4. Inside of petals—Empire Yellow, Plate 4. Reverse of petals—Pinard Yellow, Plate 4. General tonality from a distance—Empire Yellow, Plate 4.

*Discoloration.*—General tonality at end of first day—Empire Yellow, Plate 4. Second day—between Empire Yellow, Plate 4, and Pinard Yellow, Plate 4. Third day—Pinard Yellow, Plate 4.

Petals:

*Texture.*—Thick. Is not affected by wet or hot weather.

*Appearance.* — Inside — satiny; outside — shiny.

*Form.*—Oval, pointed.

*Arrangement.*—Imbricated (regularly arranged shinglelike). Petaloids in center—few; small.

*Persistence.*—Drop off cleanly.

*Fragrance.*—Moderate. Nature—tea (average hybrid tea scent).

*Lasting quality.*—On the plant and as cut flower—long.

Genital organs:

*Stamens, Anthers.*—Medium size; many. Color—Buff Yellow, Plate 4. Arrangement—regular around styles.

*Stamens, filaments (threads).*—Medium length. Color—Pale Lemon Yellow, Plate 4.

*Pollen.*—Color—Maize Yellow, Plate 4.

*Styles.*—Bunched; uneven length; short; thin.

*Stigmas.*—Color—Picric Yellow, Plate 4.

*Ovaries.*—All enclosed in calyx.

*Plant*

Form: Bush.

Growth: Dwarf; upright.

Foliage: 5 to 7 leaflets.

*Size.*—Small.

*Quantity.*—Normal.

*Color.*—New foliage—upper side: Oil Green, Plate 5, lightly overcast with Oxblood Red, Plate 1; under side: Oxblood Red, Plate 1.

Old foliage—upper side: Cress Green, Plate 31; under side: Light Cress Green, Plate 31.

*Shape.*—Oval, pointed.

*Texture.*—Upper side and under side—smooth. Ribs and veins—light.

*Edge.*—Serrated (saw-toothed).

*Serration.*—Single; small.

*Leaf stem.*—Color—Lettuce Green, Plate 5. Under side—smooth.

*Stipules.*—Short; smooth.

Wood:

*New wood.*—Color—Oil Green, Plate 5. Bark—smooth.

*Old wood.*—Color—Cerro Green, Plate 5. Bark—smooth.

Thorns:

*Quantity.*—On main stalks from base and on laterals from stalk—few.

*Form.*—Narrow base; short; straight.

*Color when young.*—Nopal Red, Plate 1.

*Position.*—Irregular.

Prickles: *Quantity.*—On main stalks and on laterals—none.

Short needles: *Quantity.*—On main stalks and on laterals—none.

I claim:

A new and distinct variety of rose plant of the large-flowered polyantha class, characterized as to novelty by its dwarf habit of plant growth, by its hybrid tea-shaped buds and flowers of Empire Yellow color in general tonality, by the long-lasting quality of its flowers on the bush outdoors, by the relatively large size of its flowers, and by its consistent blooming habit, substantially as herein shown and described.

EUGENE S. BOERNER.

No references cited.